United States Patent
Shibuya et al.

(10) Patent No.: US 9,536,319 B2
(45) Date of Patent: Jan. 3, 2017

(54) MOTION ANALYSIS METHOD, MOTION ANALYSIS DISPLAY METHOD, AND MOTION ANALYSIS DEVICE

(71) Applicant: SEIKO EPSON CORPORATION, Tokyo (JP)

(72) Inventors: Kazuhiro Shibuya, Shiojiri (JP); Kazuo Nomura, Shiojiri (JP); Kenya Kodaira, Azumino (JP); Masafumi Sato, Hara-mura (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/534,594

(22) Filed: Nov. 6, 2014

(65) Prior Publication Data
US 2015/0146933 A1  May 28, 2015

(30) Foreign Application Priority Data
Nov. 22, 2013 (JP) ................................. 2013-242192

(51) Int. Cl.
*G06K 9/00* (2006.01)
*G06T 7/20* (2006.01)
(Continued)

(52) U.S. Cl.
CPC ............... *G06T 7/20* (2013.01); *A61B 5/1122* (2013.01); *A61B 5/6895* (2013.01);
(Continued)

(58) Field of Classification Search
None
See application file for complete search history.

(56) References Cited

U.S. PATENT DOCUMENTS 5,984,798 A * 11/1999 Gilmour ............ A63B 69/3644
                                                          473/221
8,360,899 B2   1/2013 Swartz et al.
(Continued)

FOREIGN PATENT DOCUMENTS

JP    A-2008-73210    4/2008
JP    A-2009-224859   10/2009
(Continued)

OTHER PUBLICATIONS

Mar. 26, 2015 Extended European Search Report issued in European Patent Application No. 14194045.2.

*Primary Examiner* — Atiba O Fitzpatrick
*Assistant Examiner* — Carol Wang
(74) *Attorney, Agent, or Firm* — Oliff PLC

(57) ABSTRACT

A motion analysis device has a determination unit which uses an output from an inertial sensor mounted on at least one of a subject and a tool operated by the subject, to determine a dominant hand of the subject in a swing. The determination unit can determine the dominant hand on the basis of the sign of angular velocity or acceleration from the inertial sensor. A calculation unit which calculates motion analysis information in a swing, using an output from the inertial sensor can add dominant hand information from the determination unit to the motion analysis information. The motion analysis device can include a coincidence determination unit which determines that a first subject and a second subject have different dominant hands, and an inverted image generation unit which inverts first motion analysis information in the case of no coincidence.

8 Claims, 9 Drawing Sheets

(51) Int. Cl.

| | | |
|---|---|---|
| *G09B 19/00* | (2006.01) | |
| *A61B 5/00* | (2006.01) | |
| *A63B 69/36* | (2006.01) | |
| *A61B 5/11* | (2006.01) | |
| *A63B 24/00* | (2006.01) | |
| *A63B 71/06* | (2006.01) | |

(52) U.S. Cl.
CPC ...... *A63B 69/3608* (2013.01); *G09B 19/0038* (2013.01); *A61B 5/744* (2013.01); *A61B 2562/0219* (2013.01); *A63B 24/0006* (2013.01); *A63B 2071/0647* (2013.01); *A63B 2220/40* (2013.01); *A63B 2220/51* (2013.01); *A63B 2220/833* (2013.01); *G06T 2207/30221* (2013.01)

(56) References Cited

U.S. PATENT DOCUMENTS

| | | | |
|---|---|---|---|
| 8,371,962 B2 | 2/2013 | Solheim et al. | |
| 8,444,509 B2 | 5/2013 | Swartz et al. | |
| 8,747,246 B2 | 6/2014 | Swartz et al. | |
| 2003/0190972 A1 | 10/2003 | Townsend | |
| 2005/0054457 A1* | 3/2005 | Eyestone | A63B 15/00 473/221 |
| 2006/0166737 A1 | 7/2006 | Bentley | |
| 2007/0135225 A1 | 6/2007 | Nieminen et al. | |
| 2007/0298898 A1* | 12/2007 | Kiraly | A63B 69/3658 473/131 |
| 2009/0088275 A1 | 4/2009 | Solheim et al. | |
| 2010/0151956 A1 | 6/2010 | Swartz et al. | |
| 2011/0028248 A1* | 2/2011 | Ueda | A63B 69/3614 473/409 |
| 2011/0124445 A1* | 5/2011 | Uehling, III | A63B 24/0003 473/461 |
| 2013/0005496 A1 | 1/2013 | Priester et al. | |
| 2013/0035139 A1* | 2/2013 | Sheynblat | H04M 1/0281 455/566 |
| 2013/0072316 A1* | 3/2013 | Morin | A63B 69/36 473/223 |
| 2013/0260923 A1* | 10/2013 | Okazaki | G01B 7/001 473/409 |
| 2014/0200094 A1* | 7/2014 | Parke | A63F 13/00 473/223 |
| 2015/0120021 A1* | 4/2015 | Kerhuel | A63B 69/38 700/91 |

FOREIGN PATENT DOCUMENTS

| | | |
|---|---|---|
| JP | A-2009-226215 | 10/2009 |
| JP | A-2011-120611 | 6/2011 |
| JP | A-2013-111206 | 6/2013 |

* cited by examiner

MOTION ANALYSIS METHOD, MOTION ANALYSIS DISPLAY METHOD, AND MOTION ANALYSIS DEVICE

BACKGROUND

1. Technical Field

The present invention relates to a motion analysis method, a motion analysis display method, and a motion analysis device or the like.

2. Related Art

A motion analysis device is used to analyze a motion such as a swing action. As a sporting gear is swung in a swing, the posture of the sporting gear changes along time axis. An inertial sensor is installed on the sporting gear. A swing action is visually reproduced on the basis of an output from the inertial sensor. A specific example of such a motion analysis device may be, for example, a golf swing analysis device as disclosed in JP-A-2008-73210. JP-A-2008-73210 discloses mounting an inertial sensor at two positions on a golf club formed as a rigid body, such as the shaft and the head of the golf club.

Subjects have their dominant hands. For example, in a golf swing, the rotating direction of the swing action is reversed if the dominant hand is different. Therefore, in the case where motion analysis data taken with subjects with different dominant hands are compared, the rotating directions of swing trajectories are displayed as opposite directions and cannot be superimposed and compared with each other. Thus, these data are rarely used with each other in motion analysis. In the case where motion analysis data taken with subjects with different dominant hands are used with each other, dominant hand information must be provided in advance and processing to invert images or the like must be carried out.

SUMMARY

An advantage of some aspects of the invention is to provide a motion analysis method and a motion analysis device that can automatically determine the dominant hand of subject.

Another advantage of some other aspects of the invention is to provide a motion analysis display method and a motion analysis program that can display, in an inverted direction, one of motions paired with each other that are mirror images to each other because of the different dominant hands.

(1) An aspect of the invention relates to a motion analysis method including determining a dominant hand of a subject in a swing using an output from an inertial sensor mounted on at least one of the subject and a tool operated by the subject.

According to the aspect of the invention, an output from the inertial sensor can be used to find out a clear feature (for example, rotating direction or moving direction) of a motion that is unique to the dominant hand of the subject. Therefore, the dominant hand of the subject can be automatically determined on the basis of the output from the inertial sensor.

(2) In the aspect of the invention, the method may include: calculating motion analysis information in the swing, using the output from the inertial sensor, and adding information of the dominant hand to the subject of the motion analysis information.

Adding the information of the dominant hand of the subject to the motion analysis information enables the use of the information of the dominant hand of the subject when analyzing the motion on the basis of the motion analysis information.

(3) In the aspect of the invention, the motion analysis information may include first motion analysis information of a first subject, and second motion analysis information of a second subject, the information of the dominant hand of the subject may include first dominant hand information added to the first motion analysis information, and second dominant hand information added to the second motion analysis information, and the method may include determining whether the dominant hands of the first subject and the second subject coincide with each other or not, on the basis of the first dominant hand information and the second dominant hand information.

Comparing the dominant hand information added to the motion analysis information with each other enables easy and secure determination on whether the dominant hands of the first subject and the second subject coincide with each other or not.

(4) In the aspect of the invention, angular velocity obtained from the output from the inertial sensor may be used to determine the dominant hand of the subject on the basis of whether the angular velocity is positive or negative.

If the rotating direction about the detection axis of an angular velocity sensor is different, the positive and negative of the angular velocity are reversed with respect to each other. Therefore, the dominant hand of the subject can be determined on the basis of whether the angular velocity is positive or negative.

(5) In the aspect of the invention, acceleration obtained from the output from the inertial sensor may be used to determine the dominant hand of the subject on the basis of whether the acceleration is positive or negative.

If the forward and backward directions acceleration differ in the direction of the detection axis of an acceleration sensor, the positive and negative of the acceleration are reversed with respect to each other. Therefore, the dominant hand of the subject can be determined on the basis of whether the acceleration is positive or negative.

(6) Another aspect of the invention relates to a motion analysis display method for displaying a motion analysis on a first subject and a second subject as subjects including: calculating first motion analysis information of the first subject and second motion analysis information of the second subject in a swing, using an output from an inertial sensor mounted on at least one of the subject and a tool operated by the subject; determining a dominant hand of the first subject and the second subject, using the first motion analysis information and the second motion analysis information; inverting the first motion analysis information if, as a result of the determination, it is determined that the first subject and the second subject have different dominant hands; and displaying, on a screen, an image based on the first motion analysis information that is inverted.

According to the aspect of the invention, for example, one of a motion analysis result on a right-handed subject and a motion analysis result on a left-handed subject is displayed in an inverted direction. That is, a motion carried out by a left-handed person is displayed in the same direction as a motion carried out by a right-handed person. Thus, the motion carried out by the left-handed person and the motion carried out by the right-handed person can be compared with each other more easily, making the motion analysis easier.

(7) Still another aspect of the invention relates to a motion analysis display method for displaying a motion analysis on a first subject and a second subject as subjects including:

calculating first motion analysis information of the first subject and second motion analysis information of the second subject in a swing, using an output from an inertial sensor mounted on at least one of the subject and a tool operated by the subject; generating first image data based on the first motion analysis information and second image data based on the second motion analysis information, and determining a dominant hand of the first subject and the second subject, using the first motion analysis information and the second motion analysis information; and inverting the first image data if, as a result of the determination, it is determined that the first subject and the second subject have different dominant hands.

According to the aspect of the invention, for example, one of a swing trajectory by a right-handed subject and a swing trajectory by a left-handed subject is displayed in an inverted direction. That is, a motion carried out by a left-handed person is displayed in the same direction as a motion carried out by a right-handed person. Thus, the motion carried out by the left-handed person and the motion carried out by the right-handed person can be compared with each other more easily, making the motion analysis easier.

(8) In the another and still another aspects of the invention, an image based on the first motion analysis information and an image based on the second motion analysis information may be displayed, superimposed together on the screen.

The motion carried out by the left-handed person and the motion carried out by the right-handed person can be displayed, superimposed together in the same direction. Whether the two images are the same or different can be clearly grasped, making the motion analysis much easier. Also, the motion carried out by the left-handed person and the motion carried out by the right-handed person can be compared with each other more easily, making the motion analysis easier.

(9) Yet another aspect of the invention relates to a motion analysis device which determines a dominant hand of the subject in a swing, using an output from an inertial sensor mounted on at least one of a subject and a tool operated by the subject.

According to the aspect of the invention, the motion analysis method according to the one aspect of the invention can be carried out suitably and the dominant hand of the subject can be automatically determined on the basis of the output from the inertial sensor.

(10) Still yet another aspect of the invention relates to a motion analysis program for causing a computer to implement a procedure to determine a dominant hand of a subject, using an output from an inertial sensor.

(11) Further another aspect of the invention relates to a motion analysis program for causing a computer to implement procedures including: calculating first motion analysis information of a first subject and second motion analysis information of a second subject, using an output from an inertial sensor; determining a dominant hand of the first subject and the second subject, using the first motion analysis information and the second motion analysis information; determining whether the dominant hands of the first subject and the second subjects coincide with each other or not; and inverting the first motion analysis information if the dominant hands do not coincide.

(12) Still further another aspect of the invention relates to a motion analysis program for causing a computer to implement procedures including: calculating first motion analysis information of a first subject and second motion analysis information of a second subject, using an output from an inertial sensor; generating first image data based on the first motion analysis information and second image data based on the second motion analysis information; determining a dominant hand of the first subject and the second subject, using the first motion analysis information and the second motion analysis information; determining whether the dominant hands of the first subject and the second subjects coincide with each other or not; and inverting the first image data if the dominant hands do not coincide.

These motion analysis programs can cause a computer to execute the operations of the motion analysis device according to the above aspect. The programs may be stored in the motion analysis device from the beginning, or may be stored in a storage medium and installed in the motion analysis device, or may be downloaded to a communication terminal of the motion analysis device from a server via a network.

BRIEF DESCRIPTION OF THE DRAWINGS

The invention will be described hereinafter with reference to the accompanying drawings, wherein like numbers reference like elements.

DESCRIPTION OF EXEMPLARY EMBODIMENTS

Hereinafter, an embodiment of the invention will be described with reference to the accompanying drawings. The following embodiment should not unduly limit the content of the invention described in the appended claims. Not all the configurations described in this embodiment are necessarily essential as solutions provided by the invention.

1. Configuration of Golf Swing Analysis Device

Figure 1:
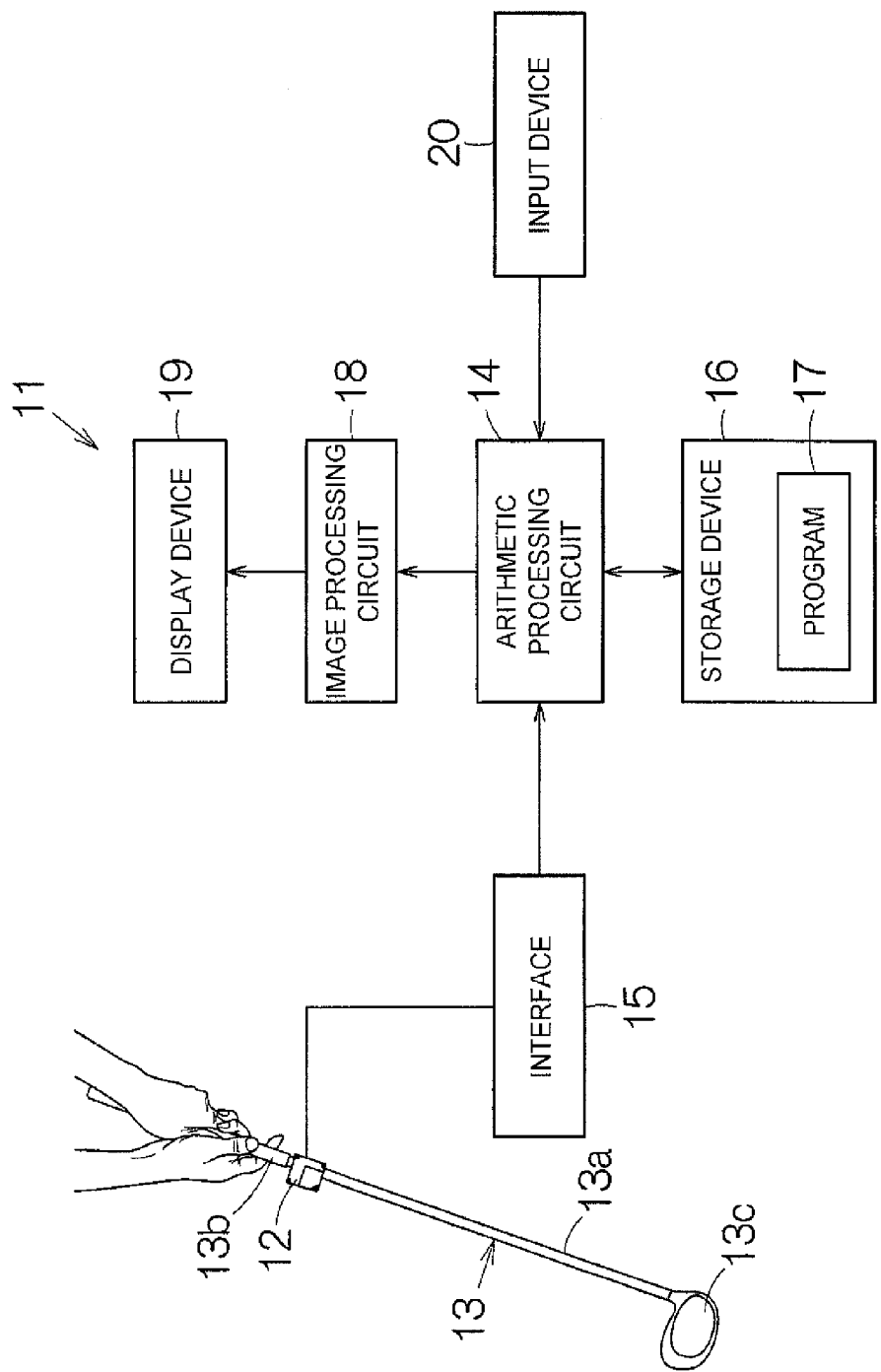
FIG. 1 is a conceptual view schematically showing the configuration of a golf swing analysis device according to an embodiment of the invention.
Figure 2:
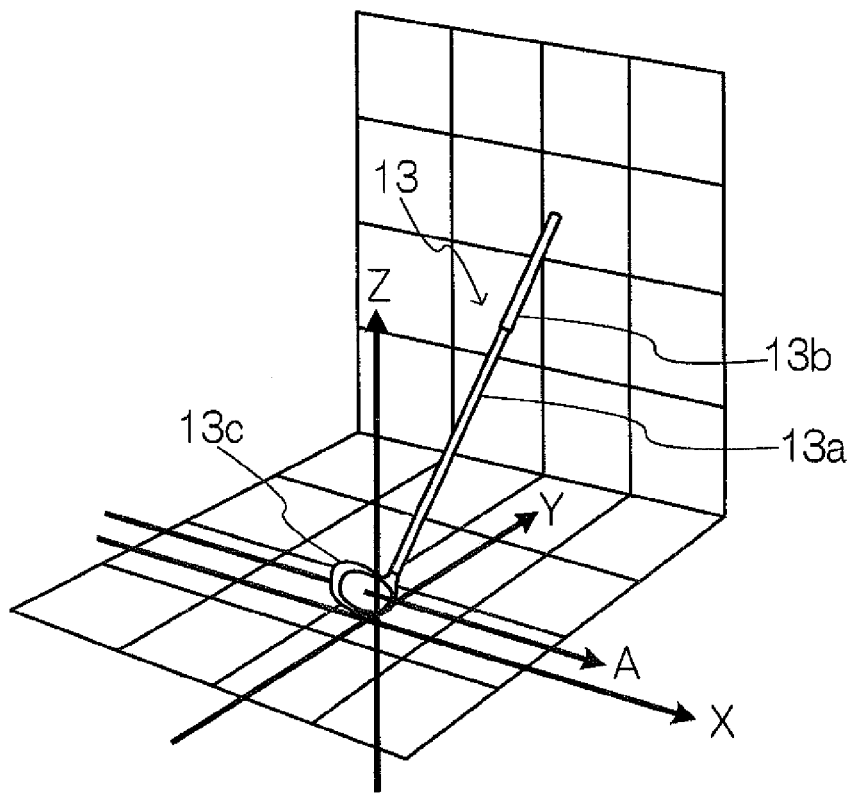
FIG. 2 illustrates an absolute coordinate system (world coordinate system) $\Sigma XYZ$.

FIG. 1 schematically shows the configuration of a golf swing analysis device (motion analysis device) 11 according to an embodiment of the invention. An inertial sensor 12 is connected to the golf swing analysis device 11. For example, an acceleration sensor and a gyro sensor are incorporated in the inertial sensor 12. The acceleration sensor can detect acceleration in each of three axial directions that are orthogonal to each other. The gyro sensor can detect angular velocity about each of the three axes that are orthogonal to each other. The inertial sensor 12 outputs a detection signal. The acceleration and angular velocity on each axis are specified by the detection signal. The acceleration sensor and the gyro sensor detect information of acceleration and velocity relatively accurately.

The inertial sensor 12 is mounted on a golf club (sporting gear) 13. The golf club 13 has a shaft 13a and a grip 13b. The grip 13b is held by the hands. The grip 13b is formed coaxially with the axis of the shaft 13a. A club head 13c is connected to the distal end of the shaft 13a. Preferably, the inertial sensor 12 is mounted on the shaft 13a or the grip 13b of the golf club 13. The shaft 13a refers to a stick-like portion up to the club head 13c, including the grip 13b. It is sufficient that the inertial sensor 12 is fixed to the golf club 13 in a relatively non-movable manner. Here, in mounting the inertial sensor 12, one of the detection axes of the inertial sensor 12 is aligned with the axis of the shaft 13a. Another one of the detection axes of the inertial sensor 12 is aligned with the direction of the face (ball hitting surface) of the club head 13c.

The golf swing analysis device 11 has an arithmetic processing circuit 14. The inertial sensor 12 is connected to the arithmetic processing circuit 14. For this connection, a predetermined interface circuit 15 is connected to the arithmetic processing circuit 14. The interface circuit 15 may be wired to the inertial sensor 12 or wirelessly connected to the inertial sensor 12. A detection signal is inputted to the arithmetic processing circuit 14 from the inertial sensor 12.

A storage device 16 is connected to the arithmetic processing circuit 14. In the storage device 16, for example, a golf swing analysis software program (motion analysis program) 17 and related data are stored. The arithmetic processing circuit 14 executes the golf swing analysis software program 17 to realize a golf swing analysis method. The storage device 16 can include a DRAM (dynamic random access memory), a large-capacity storage unit, a non-volatile memory or the like. For example, in the DRAM, the golf swing analysis software program 17 is temporarily held when carrying out the golf swing analysis method. In the large-capacity storage unit such as a hard disk drive (HDD), the golf swing analysis software program 17 and data are saved. In the non-volatile memory, a relatively small-capacity program such as BIOS (basic input/output system) and data are stored.

The arithmetic processing circuit 14 calculates a moving trajectory of a site of interest on the golf club 13, for example, the club head 13c. An image processing circuit 18 is connected to the arithmetic processing circuit 14. The arithmetic processing circuit 14 sends predetermined image data to the image processing circuit 18. A display device 19 is connected to the image processing circuit 18. For this connection, a predetermined interface circuit (not shown) is connected to the image processing circuit 18. The image processing circuit 18 sends an image signal to the display device 19, according to the image data inputted thereto. An image specified by the image signal is displayed on the screen of the display device 19. For example, a moving trajectory of the club head 13c is displayed. As the display device 19, a liquid crystal display or another type of flat panel display is used.

2. Motion Analysis Model

Figure 3:
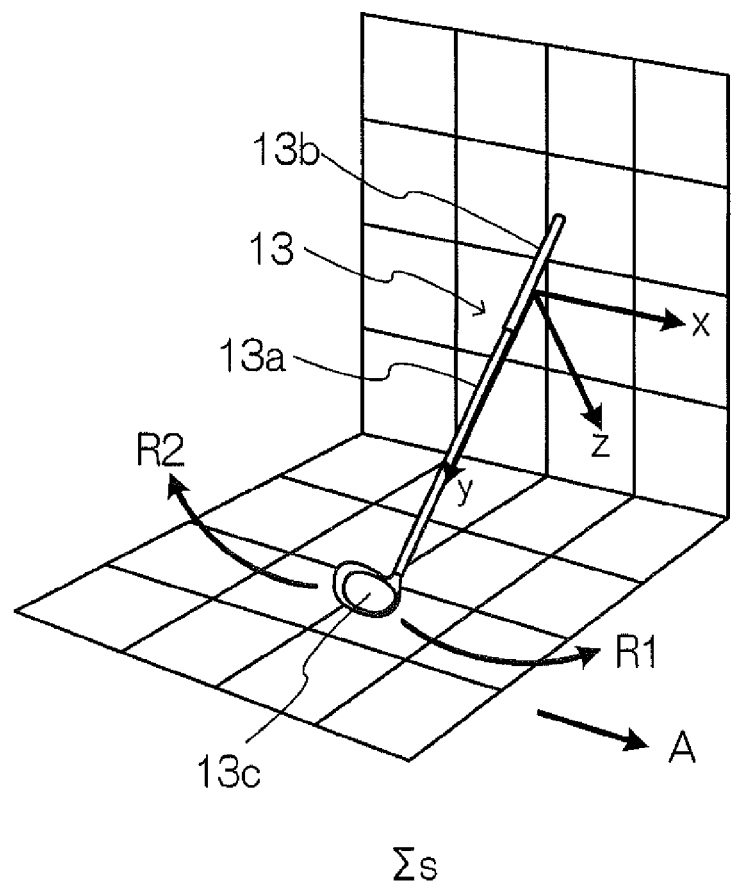
FIG. 3 illustrates a local coordinate system (sensor coordinate system) $\Sigma s$.
Figure 4:
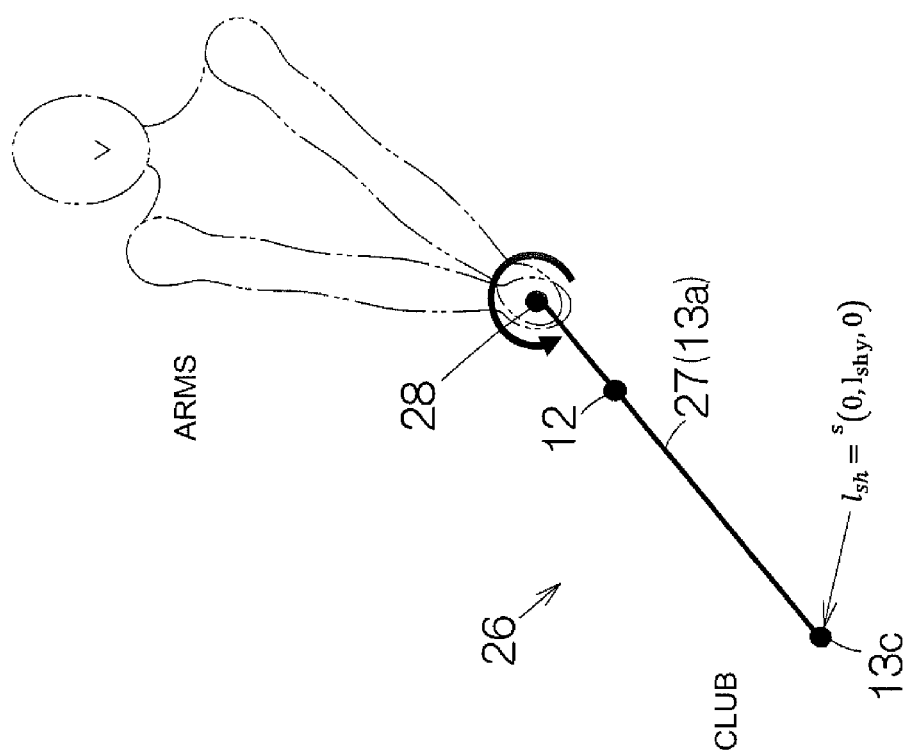
FIG. 4 is a conceptual view schematically showing the relation between a motion analysis model, and a golfer and a golf club.

In the arithmetic processing circuit 14, a three-dimensional motion analysis model 26 shown in FIG. 4 is constructed according to an absolute reference coordinate system (world coordinate system) $\Sigma XYZ$. The coordinate axes forming the absolute reference coordinate system $\Sigma XYZ$ are expressed as X-axis, Y-axis and Z-axis. The Z-axis in the absolute reference coordinate system $\Sigma XYZ$ is in vertical direction. The X-axis is in parallel to a target direction A that intersects with the face of the club head 13c. The Y-axis, orthogonal to the X-axis and Z-axis, is parallel to the direction of depth. In contrast, in a local coordinate system (sensor coordinate system) $\Sigma s$ of the inertial sensor 12, as shown in FIG. 3, the y-axis is in the direction of the longitudinal axis in which the shaft 13a extends. The x-axis is parallel to the target direction A, similarly to the X-axis. The z-axis, orthogonal to the x-axis and y-axis, is in the orthogonal downward direction to the shaft 13a. The origin of the local coordinate system $\Sigma s$ is set to the origin of the detection axes of the inertial sensor 12. The coordinate axes forming the local coordinate system $\Sigma s$ are expressed as x-axis, y-axis and z-axis.

As shown in FIG. 4, a bar 27 in the three-dimensional motion analysis model 26 is point-constrained at a support 28. The bar 27 acts as a pendulum three-dimensionally about the support 28. The position of the support 28 can be moved. Here, according to the absolute reference coordinate system $\Sigma XYZ$, the position of the distal end 13c is specified.

The three-dimensional motion analysis model 26 is equivalent to a modeling of the golf club 13 at the time of a swing. The pendulum bar 27 projects the shaft 13a of the golf club 13. The support 28 of the bar 27 projects the grip 13b. The inertial sensor 12 is fixed on the shaft 13a. The inertial sensor 12 outputs an acceleration signal and an angular velocity signal. As the acceleration signal, an acceleration signal including gravitational acceleration g is outputted.

The arithmetic processing circuit 14 similarly fixes the local coordinate system $\Sigma s$ shown in FIG. 3 to the inertial sensor 12. According to the local coordinate system $\Sigma s$ shown in FIG. 3, the position lsh of the club head 13c is specified by $(0, 1_{shy}, 0)$, as shown in FIG. 4.

3. Calculation of Swing Trajectory

Figure 5:
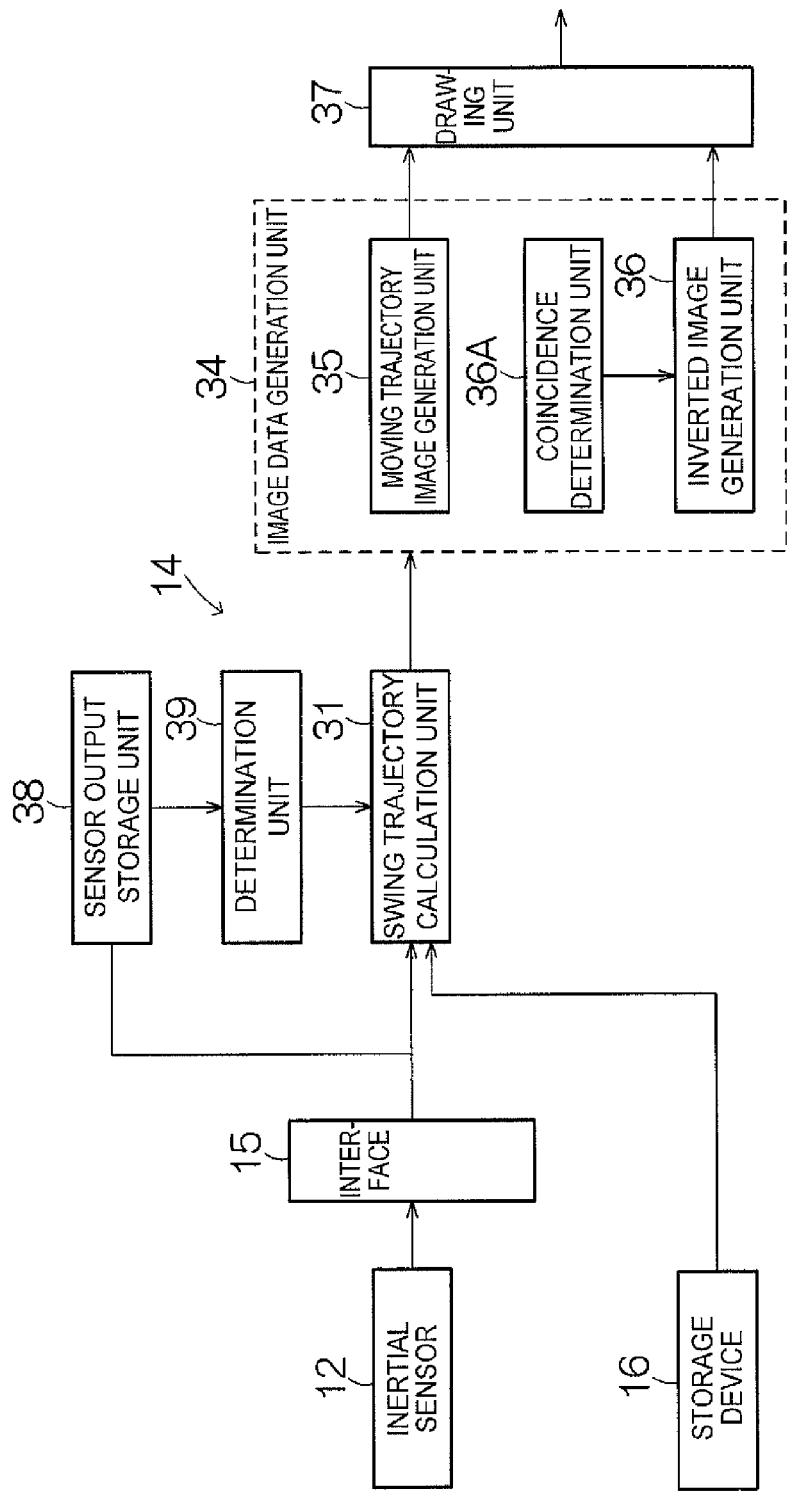
FIG. 5 is a block diagram schematically showing the configuration of an arithmetic processing circuit according to an embodiment.

FIG. 5 schematically shows the configuration of the arithmetic processing circuit 14 according to an embodiment. The arithmetic processing circuit 14 has, for example, a swing trajectory calculation unit 31 as a motion analysis unit. The swing trajectory calculation unit 31 is connected to the inertial sensor 12. An output signal is supplied to the swing trajectory calculation unit 31 from the inertial sensor 12. Here, the output from the inertial sensor 12 includes acceleration detected along each of the three orthogonal axes and angular velocity detected about each of the three orthogonal axes. The swing trajectory calculation unit 31 detects the position and posture of the golf club 13 on the basis of the output from the inertial sensor 12 and calculates moving trajectories of the golf club and the subject's arms, using various methods.

4. Display

The arithmetic processing circuit 14 has an image data generation unit 34. The image data generation unit 34 is connected to the swing trajectory calculation unit 31. An output signal is supplied to the image data generation unit 34 from the swing trajectory calculation unit 31. The image data generation unit 34 has a moving trajectory image generation unit 35, an inverted image generation unit 36, and a coincidence determination unit 36A. The moving trajectory image generation unit 35 generates an image that visually shows a moving trajectory of the golf club 13 on the basis of the position and posture of the golf club 13. The inverted image generation unit 36 generates an inverted image formed by inverting an image. The coincidence determination unit 36A determines whether dominant hand information (first and second dominant hand information) added to two pieces of motion analysis information (first and second motion analysis information) coincides with each other, and supplies the result of the determination to the inverted image generation unit 36.

The arithmetic processing circuit 14 has a drawing unit 37. The drawing unit 37 is connected to the image data generation unit 34. Image data is supplied to the drawing unit 37 from the image data generation unit 34. The drawing unit 37 draws an image that visually shows a moving trajectory of the golf club 13 on the basis of an output signal from the moving trajectory image generation unit 35. The drawing unit 37 also draws an inverted image on the basis of an output signal from the inverted image generation unit 36.

5. Determination of Dominant Hand of Subject

On a swing action of the golf club 13, the arithmetic processing circuit 14 receives an output signal from the inertial sensor 12. As shown in FIG. 5, a sensor output storage unit 38 can be provided on the subsequent stage to the interface 15, as a receiving unit for an output signal from the inertial sensor 12. An output signal from the inertial sensor 12 is stored in the sensor output storage unit 38.

A determination unit 39 is connected to the sensor output storage unit 38. The determination unit 39 determines the dominant hand of the subject on the basis of an output from the inertial sensor 12. The dominant hand information of the subject determined by the determination unit 39 is outputted to the swing trajectory calculation unit 31. The swing trajectory calculation unit 31 adds the dominant hand information of the subject to motion analysis information such as position information or the like of the club head 13c.

Figure 6:
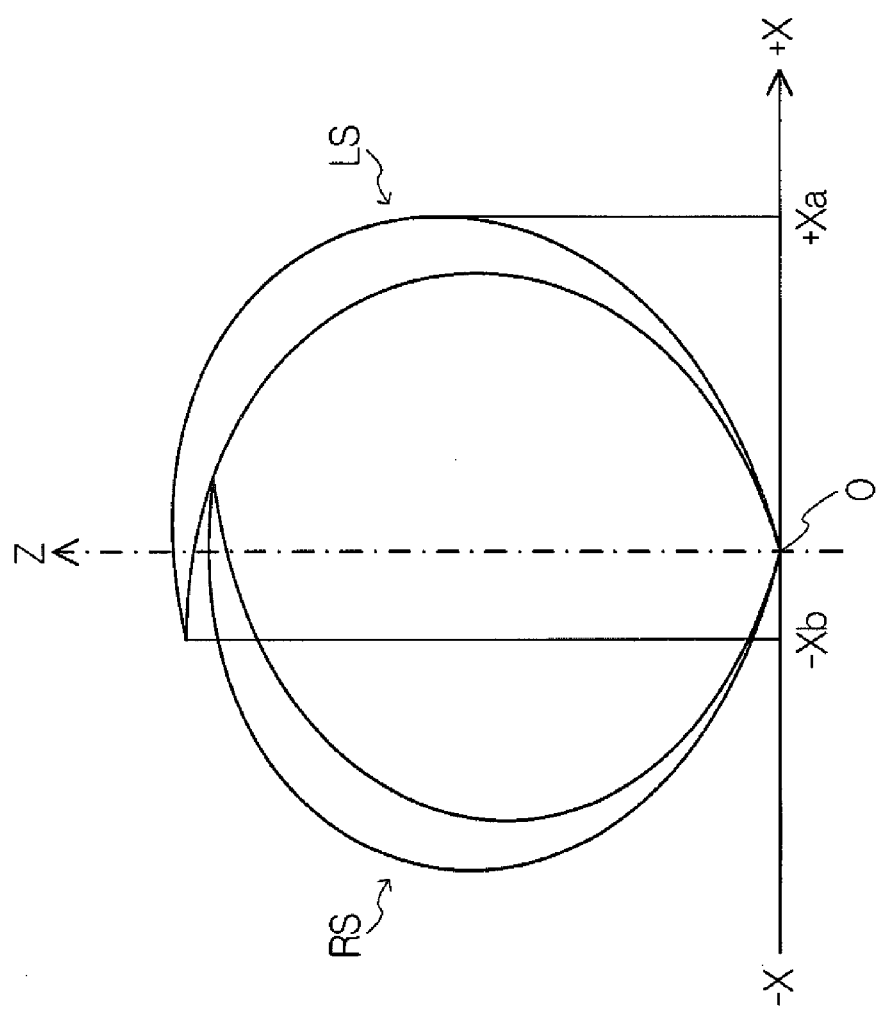
FIG. 6 illustrates an example of display showing a swing trajectory RS of a club head by a right-handed subject and a swing trajectory LS of a club head by a left-handed subject.

FIG. 6 shows an example of display in which a swing trajectory RS of the club head 13c of the golf club 13 formed by a right-handed subject and a swing trajectory LS of the club head 13c of the golf club 13 formed by a left-handed subject are projected on an X-Z plane in the absolute coordinate system ΣXYZ or displayed three-dimensionally and then viewed straight from the lateral side. In FIG. 6, the point of intersection O between the X-axis and Y-axis is at the origin on the X-axis, which is the address position (impact position) of the club head 13c. It can also be said that the swing trajectory RS and the swing trajectory LS are in the relation of mirror inversion about a reference plane including the Z-axis passing through the origin O.

The swing trajectory RS and the swing trajectory LS are substantially in the relation of mirror images to each other about the reference plane, due to the difference in the dominant hand between the subjects. In this embodiment, the determination unit 39 automatically determines whether the subject is right-handed or left-handed on the basis of an output from the inertial sensor 12.

Figure 7A:
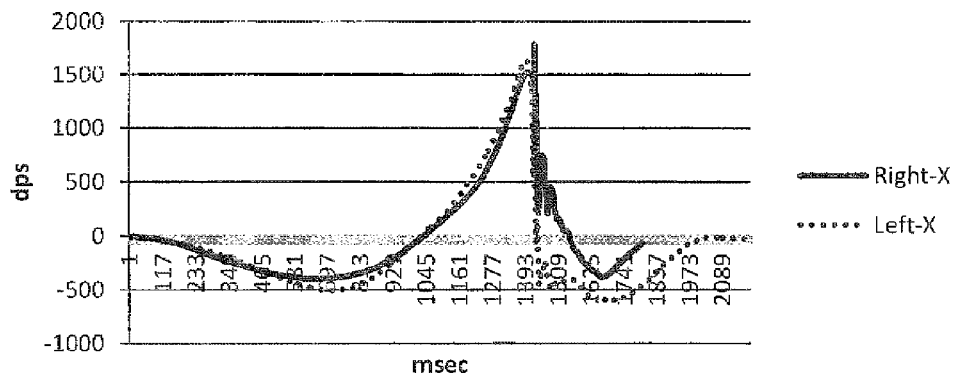
FIGS. 7A to 7C show time series data of angular velocity about x-axis, y-axis and z-axis, as an output from an inertial sensor.
Figure 7B:
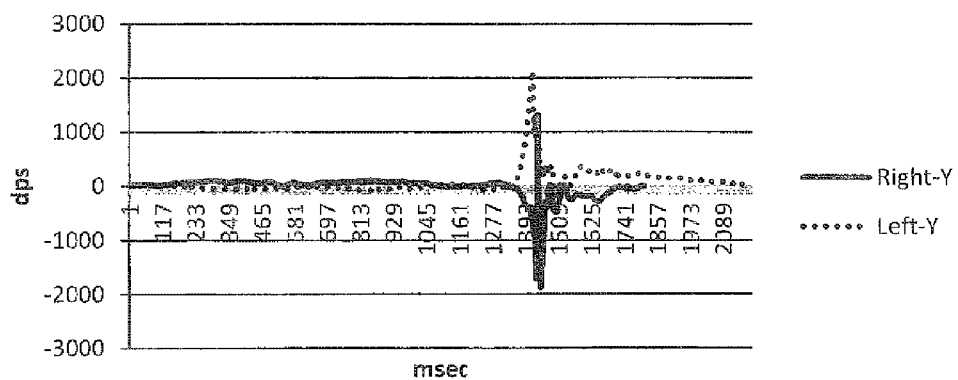
Figure 7C:
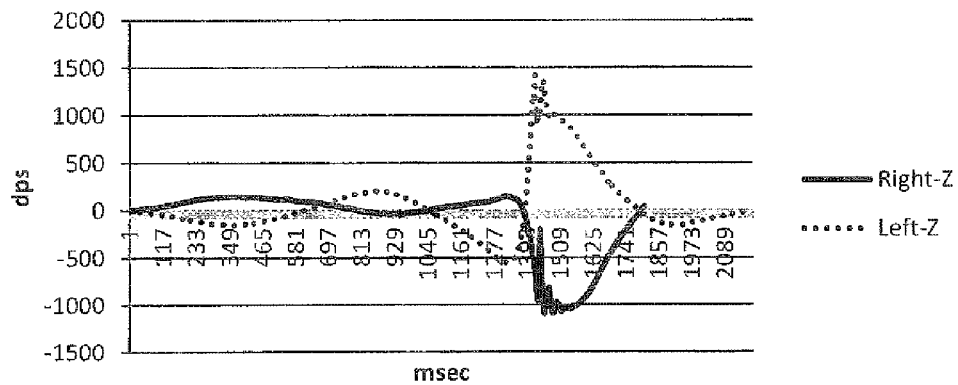
Figure 8A:
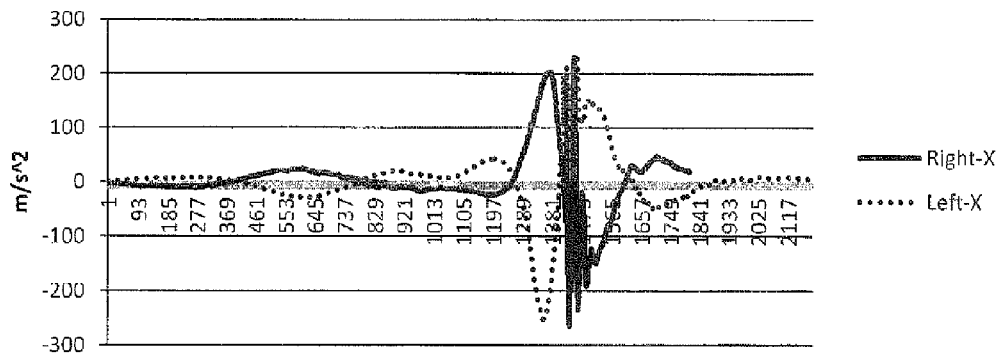
FIGS. 8A to 8C show time series data of acceleration in the directions of x-axis, y-axis and z-axis, as an output from an inertial sensor.
Figure 8B:
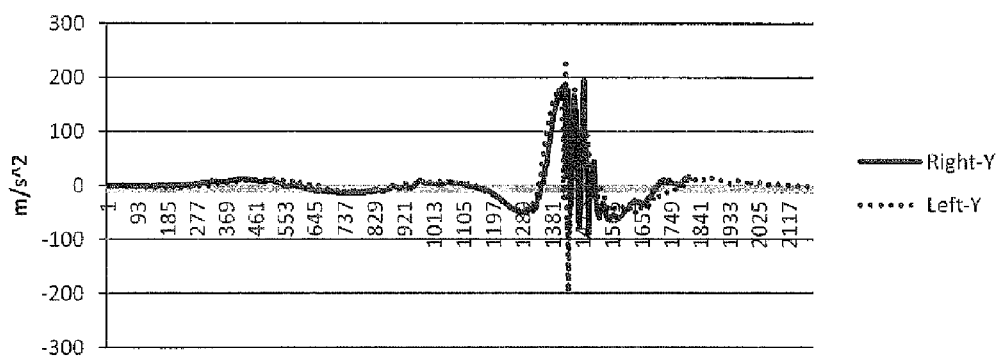
Figure 8C:
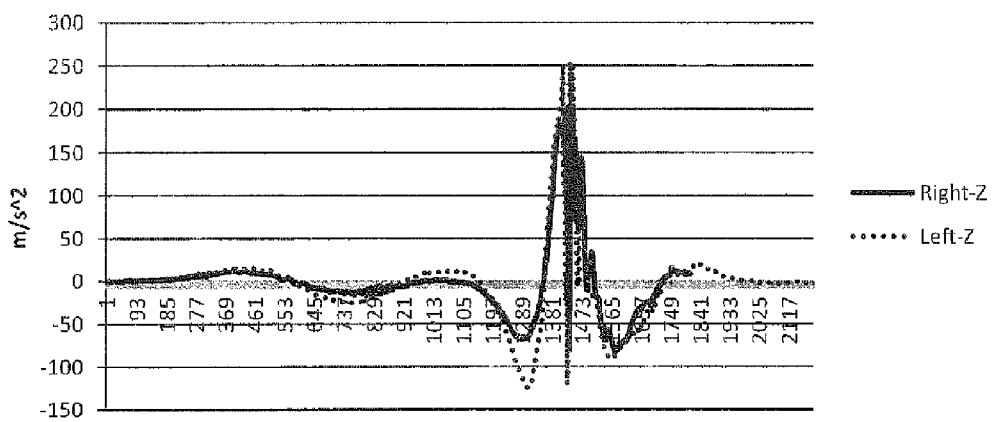

FIGS. 7A to 7C and FIGS. 8A to 8C show time series data of six components, respectively, as an output from the inertial sensor 12. FIGS. 7A to 7C show time series data of angular velocity about the x-axis, y-axis and z-axis of a three-axis angular velocity sensor. FIGS. 8A to 8C show time series data of acceleration in the direction of the x-axis, y-axis and z-axis of a three-axis acceleration sensor.

First, the angular velocity data is considered. The angular velocity about the z-axis shown in FIG. 7C manifests the inverted relation between right-handedness and left-handedness most notably. The reason for this is clear from FIG. 3. The output data from the inertial sensor 12 is gathered about the three axes xyz in the local coordinate system Σs shown in FIG. 3 as references. As shown in FIG. 3, in the behavior of the club head 13c in a swing, a turn in the R1 direction or R2 direction is the greatest motion and the rotation axis of the motion is the z-axis. That is, the motion of the club head 13c in a swing is a motion accompanying angular velocity about the z-axis. Also, in this motion, the downswing by the right-handed subject is a turn in the R1 direction, whereas the downswing by the left-handed subject is a turn in the R2 direction, that is, opposite to the R1 direction. Therefore, the angular velocity about the z-axis shown in FIG. 7C shows the relation in which the positive and negative are inverted between right-handedness and left-handedness.

In contrast, the angular velocity about the x-axis shown in FIG. 7A is almost the same between right-handedness and left-handedness. With respect to the angular velocity about the y-axis shown in FIG. 7B, the sign is substantially inverted between right-handedness and left-handedness. However, the degree of inversion varies depending on the swing.

Based on the above, it can be understood that the determination unit 39 is able to determine whether the subject is right-handed or left-handed on the basis of the angular velocity data from the inertial sensor 12, and is sufficiently able to determine whether the subject is right-handed or left-handed particularly on the basis of the time series data of angular velocity about the z-axis shown in FIG. 7C.

Next, the acceleration data is considered. The acceleration in the x-axis direction shown in FIG. 8A manifests the inverted relation between right-handedness and left-handedness most notably. The reason for this is clear from FIG. 3. As shown in FIG. 3, in the behavior of the club head 13c in a swing, the x-axis parallel to the target direction A is the direction of a tangent line for a swing turn. Therefore, a swing turn is a motion in which the acceleration on the x-axis is the greatest of the three axes. That is, the motion of the club head 13c in a swing is a motion accompanying acceleration in the x-axis direction. Also, in this motion, the downswing by the right-handed subject has acceleration facing the +X direction, whereas the downswing by the left-handed subject has acceleration facing the −X direction, that is, opposite to the +X direction. Therefore, the acceleration in the x-axis direction shown in FIG. 8A shows the relation in which the positive and negative are inverted between right-handedness and left-handedness.

In contrast, the acceleration in the y-axis and z-axis directions shown in FIGS. 8B and 8C is almost the same between right-handedness and left-handedness. Based on the above, it can be understood that the determination unit 39 is able to determine whether the subject is right-handed or left-handed on the basis of the acceleration data from the inertial sensor 12, and is sufficiently able to determine whether the subject is right-handed or left-handed particularly on the basis of the time series data of acceleration parallel to the x-axis shown in FIG. 8A.

6. Image Inversion

Motion analysis information corresponding to one (for example, LS) of motions paired with each other (RS, LS) that form mirror images due to the difference in the dominant hand between the subjects shown in FIG. 6 is calculated by the swing trajectory calculation unit 31 on the basis of an output from the inertial sensor 12 and inputted to the inverted image generation unit 36 shown in FIG. 5. The inverted image generation unit 36 inverts the sign (+, −) of the value of the one motion analysis information and thus enables one (for example, LS) of motions paired with each other (RS, LS) to be displayed as an inverted image (/LS) as shown in FIG. 9.

Figure 9:
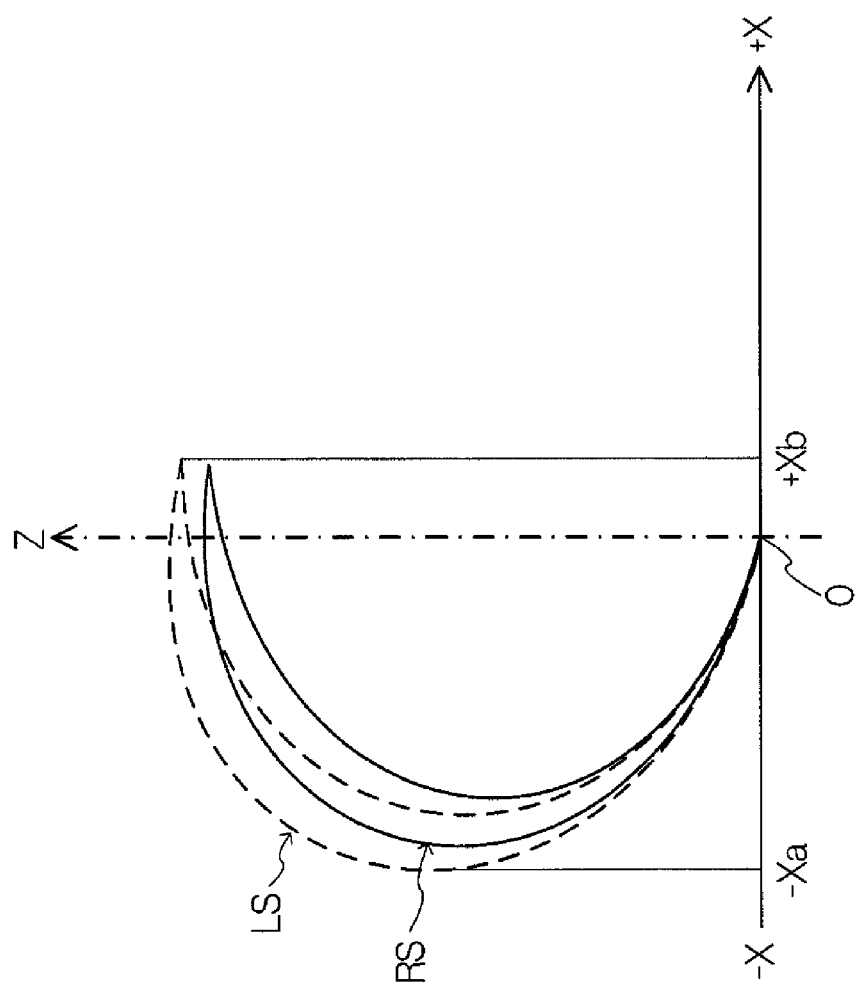
FIG. 9 shows an example of display in which one swing trajectories that are mirror images to each other due to the difference in the dominant hand of the subject is inverted, while the other is not inverted, and then the swing trajectories are superimposed together.

Thus, as shown in FIG. 9, one (for example, LS) of motions paired with each other (RS, LS) is displayed in an inverted direction on the side where the other (RS) of the motions paired with each other (RS, LS) is displayed. That is, for example, a motion carried out by a left-handed person is displayed in the same direction as an image of a motion carried out by a right-handed person. Thus, the motion carried out by the left-handed person and the motion carried out by the right-handed person can be compared with each other more easily, and motion analysis becomes easier.

If both of motions paired with each other (RS, LS) are inputted, first motion analysis information and second motion analysis information are calculated by the swing trajectory calculation unit 31, using an output from the inertial sensor 12. The inverted image generation unit 36 of the image data generation unit 34 inverts one (for example, LS) of the first motion analysis information and the second motion analysis information and leaves the other (RS) non-inverted, and thus enables the inverted image of the one (for example, /LS) and the non-inverted image (RS) of the other (for example, RS), of the motions paired with each other (RS, LS), to be superimposed together as these images are displayed on the screen as shown in FIG. 9.

This enables the motion by the left-handed person to be superimposed on and in the same direction as the motion by the right-handed person, as these motions are displayed. Thus, whether the two images are the same or different can be grasped clearly and motion analysis becomes much easier.

In the above-described example, dominant hands are determined using an output from the inertial sensor 12, and if the dominant hands are different, the inverted image generation unit 36 inverts the sign (+, −) of the value of one motion analysis information, and the one (for example, LS) of the motions paired with each other (RS, LS) is displayed as an inverted image (/LS) as shown in FIG. 9.

As another modification example, image data may be generated without inverting the sign of the value of motion analysis information, and the image data of one of the swing trajectories may be inverted if the dominant hands are determined as different. For example, the coincidence determination unit 36A of the image data generation unit 34 can determine whether images are of different dominant hands or not. If the dominant hand information added to the motion analysis information does not coincide between the two images, the coincidence determination unit 36A can instruct the inverted image generation unit 36 to invert one of the images.

The inverted image generation unit 36 inverts the sign of a position coordinate on the screen. For example, the coordinate +Xa of the image LS shown in FIG. 6 has its sign inverted to the coordinate −Xa in the inverted image /LS shown in FIG. 9. For example, the coordinate −Xb of the image LS shown in FIG. 6 has its sign inverted to the coordinate +Xb in the inverted image /LS shown in FIG. 9. In this manner, an inverted image can be easily generated, simply by inverting the sign of the X-coordinate in the absolute reference coordinate system (world coordinate system) $\Sigma XYZ$.

While the embodiment is described above in detail, a person skilled in the art can readily understand that a number of modifications can be made without substantially departing from the new matters and advantageous effects of the invention. Therefore, all such modifications are included in the scope of the invention. For example, in the specification and drawings, a term described along with a different term with a broader meaning or the same meaning at least once can be replaced with the different term in any part of the specification and drawings. Also, the configurations and operations of the inertial sensor 12, the arithmetic processing circuit 14, the three-dimensional motion analysis model 26, the swing trajectory calculation unit 31, the image data generation unit 34, the moving trajectory image generation unit 35, the inverted image generation unit 36, the coincidence determination unit 36A, the storage unit 38 and the determination unit 39 or the like are not limited to those described in the embodiment, and various modifications can be made. Also, the motion analysis to which the invention is applied is not limited to golf and can also be suitably carried out particularly with hitting or striking tools used in tennis, table tennis and the like.

The entire disclosure of Japanese Patent Application No. 2013-242192, filed Nov. 22, 2013 is expressly incorporated by reference herein.

What is claimed is:

1. A motion analysis method comprising
    determining a dominant hand of a subject in a swing using an output from an inertial sensor mounted on at least one of the subject and a tool operated by the subject;
    calculating motion analysis information in the swing, using the output from the inertial sensor; and
    adding information of the dominant hand of the subject to the motion analysis information, wherein:
        the motion analysis information includes first motion analysis information of a first subject, and second motion analysis information of a second subject,
        the information of the dominant hand of the subject includes first dominant hand information added to the first motion analysis information, and second dominant hand information added to the second motion analysis information,
        the method includes determining whether the dominant hands of the first subject and the second subject coincide with each other or not, on the basis of the first dominant hand information and the second dominant hand information,
        the inertial sensor includes an angular velocity sensor, and
        when a direction crossing a striking surface of the tool is an X axis, a longitudinal direction of the tool is a Y axis and a direction perpendicular to the X axis and the Y axis is a Z axis and when determining whether the dominant hand of the first subject matches the dominant hand of the second subject, a detection is made about whether the subject is right-handed or left-handed using an angular velocity about the Z axis detected by the angular velocity sensor when the tool is swung.

2. The motion analysis method according to claim 1, wherein angular velocity obtained from the output from the inertial sensor is used to determine the dominant hand of the subject on the basis of whether the angular velocity is positive or negative.

3. The motion analysis method according to claim 1, wherein acceleration obtained from the output from the inertial sensor is used to determine the dominant hand of the subject on the basis of whether the acceleration is positive or negative.

4. The motion analysis method according to claim 1, wherein the detection is made about whether the subject is right-handed or left-handed using time series data of the angular velocity about the Z axis detected by the angular velocity sensor when the tool is swung.

5. A motion analysis display method for displaying a motion analysis on a first subject and a second subject as subjects, the method comprising:
- calculating first motion analysis information of the first subject and second motion analysis information of the second subject in a swing, using an output from an inertial sensor mounted on at least one of the first subject and the second subject and a tool operated by the first subject and the second subject;
- determining a dominant hand of the first subject and the second subject, using the first motion analysis information and the second motion analysis information;
- inverting a positive and negative of an output of the first motion analysis information if, as a result of the determination, it is determined that the first subject and the second subject have different dominant hands; and
- displaying, on a screen, an image based on the first motion analysis information that is inverted, wherein:
  - the inertial sensor includes an angular velocity sensor, and
  - when a direction crossing a striking surface of the tool is an X axis, a longitudinal direction of the tool is a Y axis and a direction perpendicular to the X axis and the Y axis is a Z axis and when determining the dominant hand of the first subject and the second subject, a detection is made about whether the first subject and the second subject is right-handed or left-handed using an angular velocity about the Z axis detected by the angular velocity sensor when the tool is swung.

6. The motion analysis display method according to claim 5, wherein an image based on the first motion analysis information and an image based on the second motion analysis information are displayed on a same screen.

7. A motion analysis display method for displaying a motion analysis on a first subject and a second subject as subjects, the method comprising:
- using an output from an inertial sensor mounted on at least one of the first subject and the second subject and a tool operated by the first subject and the second subject, to calculate first motion analysis information of the first subject and second motion analysis information of the second subject in a swing;
- generating first image data based on the first motion analysis information and second image data based on the second motion analysis information, using the first motion analysis information and the second motion analysis information;
- determining a dominant hand of the first subject and the second subject, using the first motion analysis information and the second motion analysis information; and
- inverting the first image data if, as a result of the determination, it is determined that the first subject and the second subject have different dominant hands, wherein:
  - the inertial sensor includes an angular velocity sensor, and
  - when a direction crossing a striking surface of the tool is an X axis, a longitudinal direction of the tool is a Y axis and a direction perpendicular to the X axis and the Y axis is a Z axis and when determining the dominant hand of the first subject and the second subject, a detection is made about whether the first subject and the second subject is right-handed or left-handed using an angular velocity about the Z axis detected by the angular velocity sensor when the tool is swung.

8. The motion analysis display method according to claim 7, wherein an image based on the first motion analysis information and an image based on the second motion analysis information are displayed on a same screen.

* * * * *